United States Patent
Nakano

(10) Patent No.: US 10,366,488 B2
(45) Date of Patent: Jul. 30, 2019

(54) IMAGE PROCESSING USED TO ESTIMATE ABNORMALITIES

(71) Applicant: International Business Machines Corporation, Armonk, NY (US)

(72) Inventor: Hiroki Nakano, Otsu (JP)

(73) Assignee: International Business Machines Corporation, Armonk, NY (US)

(*) Notice: Subject to any disclaimer, the term of this patent is extended or adjusted under 35 U.S.C. 154(b) by 87 days.

(21) Appl. No.: 15/200,140

(22) Filed: Jul. 29, 2016

(65) Prior Publication Data

US 2017/0294014 A1 Oct. 12, 2017

(30) Foreign Application Priority Data

Apr. 8, 2016 (JP) ................... 2016 078506

(51) Int. Cl.
 *G06K 9/46* (2006.01)
 *G06K 9/00* (2006.01)
 (Continued)

(52) U.S. Cl.
 CPC .......... *G06T 7/0012* (2013.01); *A61B 6/037* (2013.01); *A61B 6/5217* (2013.01); *G06K 9/0014* (2013.01); *G06K 9/00147* (2013.01); *G06K 9/4628* (2013.01); *G06K 9/6256* (2013.01); *G06N 3/04* (2013.01); *G06N 3/08* (2013.01);
 (Continued)

(58) Field of Classification Search
 None
 See application file for complete search history.

(56) References Cited

U.S. PATENT DOCUMENTS

| 2002/0186882 A1* | 12/2002 | Cotman | G06K 9/00127 382/165 |
| 2006/0280348 A1* | 12/2006 | Smith | G06T 7/0012 382/128 |
| 2012/0163693 A1 | 6/2012 | Suri | |

FOREIGN PATENT DOCUMENTS

| JP | 2002325754 A | 11/2002 |
| JP | 2002330951 A | 11/2002 |

(Continued)

OTHER PUBLICATIONS

Santosh KC, Vajda S, Antani S, Thoma GR. Edge map analysis in chest X-rays for automatic pulmonary abnormality screening. International journal of computer assisted radiology and surgery. Mar. 19, 2016; 1637-46.*

(Continued)

*Primary Examiner* — Vu Le
*Assistant Examiner* — Tracy Mangialaschi
(74) *Attorney, Agent, or Firm* — Reza Sarbakhsh; SVL IPLaw

(57) ABSTRACT

An image processing apparatus includes a computer system comprising an image acquiring section that acquires an image of body tissue. An extracting section of the computer system extracts an outline of the body tissue from the image, and a converting section of the computer system converts a coordinate sequence of the outline into a value sequence. An estimating section of the computer system estimates an abnormal shape of the body tissue by performing neural network processing on the value sequence. In addition, present invention embodiments include a computer program product used by the image processing apparatus and an image processing method performed by the image processing apparatus.

20 Claims, 9 Drawing Sheets

(51) Int. Cl.
  *G06T 7/00* (2017.01)
  *G06K 9/62* (2006.01)
  *A61B 6/00* (2006.01)
  *A61B 6/03* (2006.01)
  *G06N 3/08* (2006.01)
  *G06N 3/04* (2006.01)
  *G06T 7/50* (2017.01)

(52) U.S. Cl.
  CPC .............. *G06T 7/50* (2017.01); *A61B 6/032* (2013.01); *G06T 2207/10081* (2013.01); *G06T 2207/20081* (2013.01); *G06T 2207/20084* (2013.01); *G06T 2207/30061* (2013.01)

(56) References Cited

FOREIGN PATENT DOCUMENTS

| | | | | |
|---|---|---|---|---|
| JP | 2013052256 | A | 3/2013 | |
| JP | 2014195740 | A | 10/2014 | |
| JP | 2015144929 | A | 8/2015 | |
| WO | 2015054666 | A1 | 4/2015 | |
| WO | WO 2015054666 | A1 * | 4/2015 | .......... G06N 3/0427 |

OTHER PUBLICATIONS

Scott, James A., Edwin L. Palmer, and Alan J. Fischman. "How well can radiologists using neural network software diagnose pulmonary embolism?." American Journal of Roentgenology 175.2 (2000): 399-405.*

Scott, James A. "Artificial neural networks and image interpretation: a ghost in the machine." Seminars in Ultrasound, CT and MRI. vol. 25. No. 5. WB Saunders, 2004.*

Kass, David A., et al. "Abnormalities of dynamic ventricular shape change in patients with aortic and mitral valvular regurgitation: assessment by Fourier shape analysis and global geometric indexes." Circulation research 62.1 (1988): 127-138.*

Hundal, H. S., et al. "Particle shape characterization using image analysis and neural networks." Powder technology 91.3 (1997): 217-227.*

Das, Arpita, et al. "Classification of poor contrast mammograms using a novel and fast boundary detection technique." Bioinformatics and Biomedicine Workshops (BIBMW), 2011 IEEE International Conference on. IEEE, 2011.*

Orozco, Hiram Madero, et al. "Automated system for lung nodules classification based on wavelet feature descriptor and support vector machine." Biomedical engineering online 14.1 (2015): 9.*

Granlund, Gösta H. "Fourier preprocessing for hand print character recognition." IEEE transactions on computers 100.2 (1972): 195-201.*

Zahn, Charles T., and Ralph Z. Roskies. "Fourier descriptors for plane closed curves." IEEE Transactions on computers 100.3 (1972): 269-281.*

Ramteke et al., "Analysis of Skin Cancer Using Fuzzy and Wavelet Technique—Review & Proposed New Algorithm." International Journal of Engineering Trends and Technology (IJETT), vol. 4, Issue 6, Jun. 2013, pp. 2555-2566.

Shirazinodeh et al., "Detection and classification of Breast Cancer in Wavelet Sub-bands of Fractal Segmented Cancerous Zones." J Med Signals Sens, Jul.-Sep. 2015, 10 pages.

Jacobs et al., "LUng Nodule Analysis 2016." Consortium for Open Medical Image Computing, http://luna16.grand-challenge.org/, 2012-2016, 1 page.

* cited by examiner

IMAGE PROCESSING USED TO ESTIMATE ABNORMALITIES

BACKGROUND

Technical Field

The present invention relates to an image processing apparatus, a computer program product, and an image processing method used to estimate abnormalities, for example, based on an image.

Related Art

A technique is known for judging whether cancer is present, for example, from an image of a biological organ by using a neural network, as shown in, for example, International Publication WO 2015/054666.

However, the amount of data in an image of a biological organ is too great to be processed by a neural network. On the other hand, there is a concern that compressing the number of pixels in the image, for example, in order to reduce the amount of data would reduce the accuracy of the judgment.

SUMMARY

According to a first aspect of the present invention, provided is an image processing apparatus comprising a computer system comprising an image acquiring section that acquires an image of body tissue; an extracting section that extracts an outline of the body tissue from the image; a converting section that converts a coordinate sequence of the outline into a value sequence; and an estimating section that estimates an abnormal shape of the body tissue by performing neural network processing on the value sequence. Also provided is a computer program product used by the image processing apparatus and an image processing method performed by the image processing apparatus.

The summary clause does not necessarily describe all necessary features of the embodiments of the present invention. The present invention may also be a sub-combination of the features described above.

DETAILED DESCRIPTION

Hereinafter, some embodiments of the present invention will be described. The embodiments do not limit the invention according to the claims, and all the combinations of the features described in the embodiments are not necessarily essential to components provided by aspects of the invention.

Figure 1:
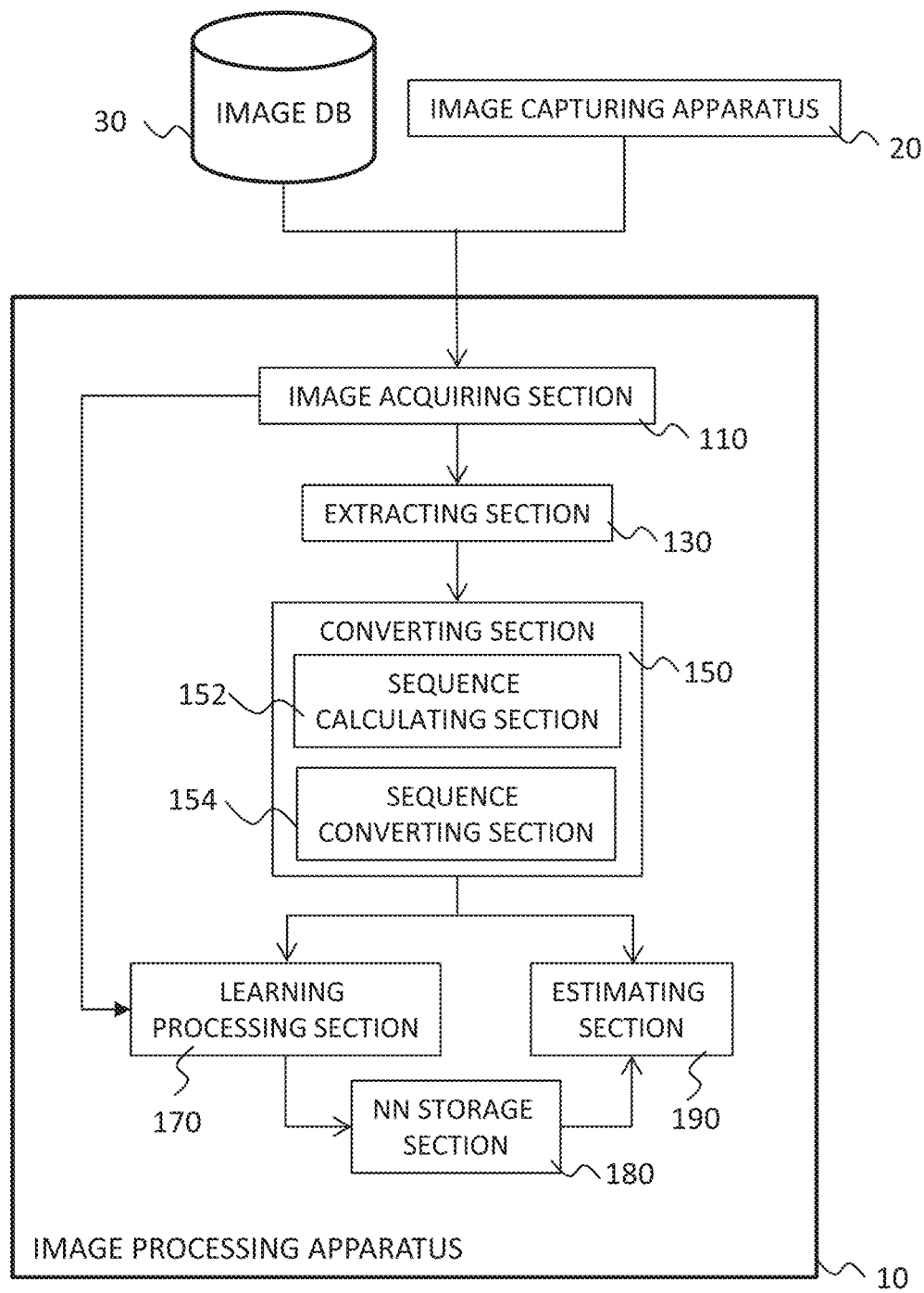
FIG. 1 is a block diagram of an image processing apparatus according to an embodiment of the present invention.

FIG. 1 is a block diagram of an image processing apparatus 10 according to an embodiment of the present invention. The image processing apparatus 10 extracts an outline of body tissue from an image of body tissue and analyzes a value sequence corresponding to this outline, thereby estimating whether an abnormal shape indicative of a disease is present in the outline portion of the body tissue. The image processing apparatus 10 includes an image acquiring section 110, an extracting section 130, a converting section 150, a learning processing section 170, a neural network storage section 180, and an estimating section 190.

The image acquiring section 110 acquires an image of the body tissue. For example, the image acquiring section 110 acquires an image of the body tissue (e.g., a CT image of a cross section of a lung) captured by an image capturing apparatus 20 (e.g., a CT apparatus). As another example, the image acquiring section 110 may acquire learning data that includes a plurality of groups of images of body tissue and abnormal shape judgment results from an image database 30. The image acquiring section 110 supplies the extracting section 130 with the images of the body tissue included in the learning data and the image of the body tissue received from the image capturing apparatus 20, and supplies the learning processing section 170 with the judgment results included in the learning data.

The extracting section 130 extracts the outline of the body tissue from the acquired image of the body tissue. The extracting section 130 supplies the converting section 150 with the extracted outline of the body tissue.

The converting section 150 includes a sequence calculating section 152 and a sequence converting section 154, and uses the sequence calculating section 152 and the sequence converting section 154 to convert a coordinate sequence of the outline into a value sequence that includes characteristics of the outline.

The sequence calculating section 152 calculates an object sequence, which is a sequence of objects to be converted into the value sequence, based on the coordinate sequence of each of the points tracing around the outline. For example, the sequence calculating section 152 calculates the object sequence to be relative coordinate values that are relative to reference coordinates of each point tracing around the outline. Detailed processing performed by the sequence calculating section 152 is described further below.

The sequence converting section 154 converts the object sequence calculated by the sequence calculating section 152 into the value sequence. For example, the sequence converting section 154 converts the object sequence into the value sequence by extracting a minor fluctuation component from the object sequence received from the sequence calculating section 152. Detailed processing performed by the sequence converting section 154 is described further below. The sequence converting section 154 supplies the learning processing section 170 and the estimating section 190 with the value sequence resulting from the conversion.

The learning processing section 170 uses the learning data to train a neural network for outputting abnormal shape judgment results. For example, the learning processing section 170 trains a neural network that receives the value sequence obtained as a result of the processing by the extracting section 130 and the converting section 150 from the image of the body tissue as input, and outputs a judgment result indicating whether an abnormal shape, as determined by a doctor or the like, is present (e.g., a judgment indicating the inclusion of an abnormal shape caused by a malignant tumor). In this learning, the learning processing section 170 may determine various parameters such as the parameters of output functions between each neuron and weighting between each neuron in the neural network. The learning processing section 170 stores the trained neural network in the neural network storage section 180.

The estimating section 190 estimates abnormal shapes of the body tissue by using the neural network to process the value sequence converted by the processing of the extracting section 130 and the converting section 150 based on the image of the body tissue acquired from the image capturing apparatus 20. For example, the estimating section 190 uses the neural network trained by the learning processing section 170 and stored in the neural network storage section 180 to estimate whether there is an abnormal shape in the body tissue (e.g., whether the body tissue in the image includes an abnormal shape caused by a malignant tumor), based on the value sequence.

In this way, with the image processing apparatus 10 according to the present embodiment, the image of the body tissue is converted into a value sequence including characteristics of the outline and neural network processing is performed on this value sequence. Therefore, compared to a case in which the image of the body tissue is processed by the neural network as-is, the image processing apparatus 10 can reduce the amount of calculation when estimating abnormal shapes.

Figure 2:
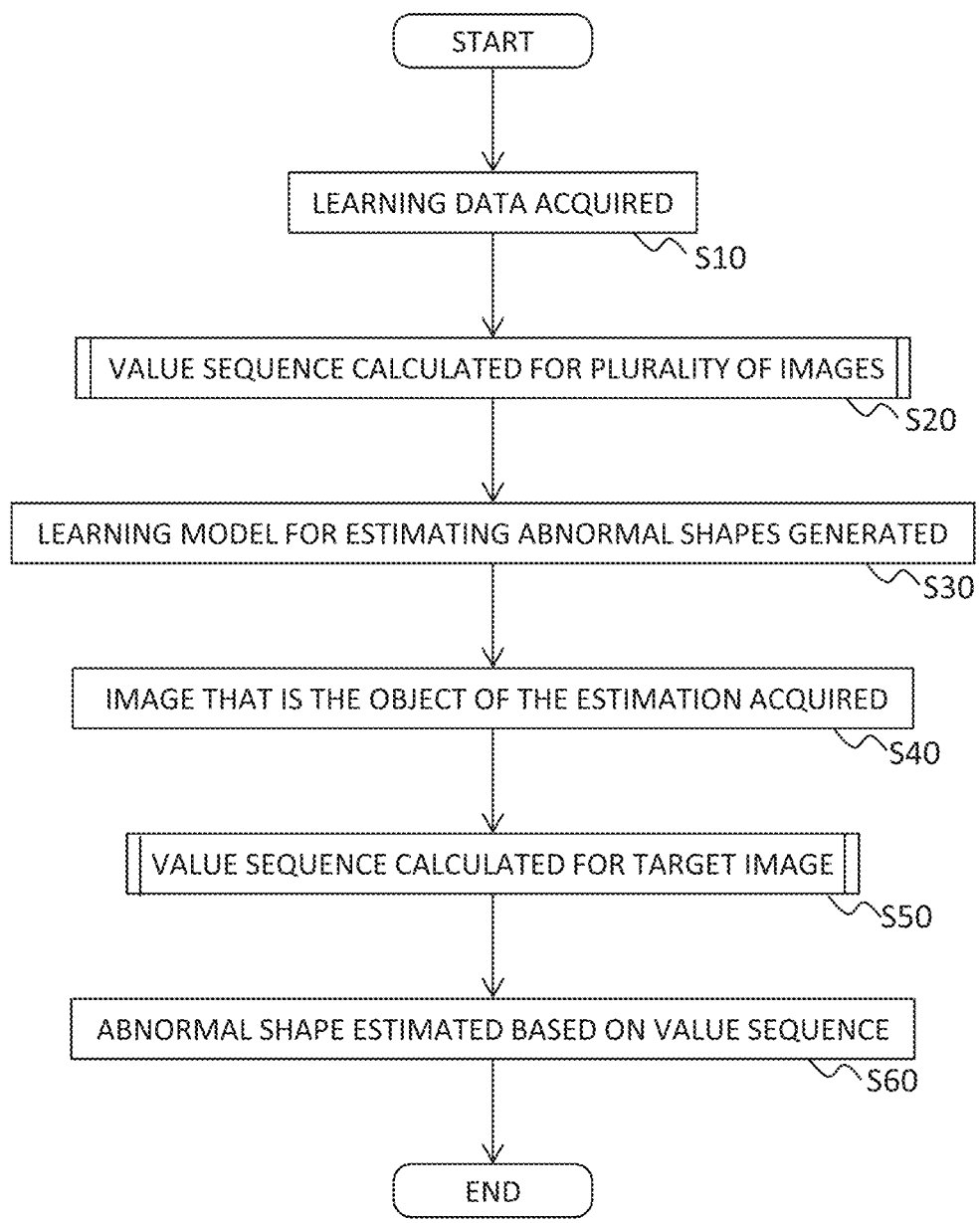
FIG. 2 shows an example process flow of the image processing apparatus according to the present invention.

FIG. 2 shows an example process flow of the image processing apparatus 10 according to the present invention. In the present embodiment, the image processing apparatus 10 performs the processing from S10 to S60 in order to train the neural network for estimating the abnormal shapes from an image of the body tissue and to estimate abnormal shapes based on this neural network.

First, at S10, the image acquiring section 110 acquires the learning data from the image database 30. The learning data may include a plurality of groups of images of body tissue and abnormal shape judgment results.

For example, the images of the body tissue may be cross-sectional images of body tissue, and can be exemplified by an image obtained by performing at least one of X-ray imaging, CT (Computed Tomography), MRI (Magnetic Resonance Imaging), PET (Positron Emission Tomography), and the like on the brain, lungs, liver, digestive tissue, or other organ or tissue of a human or animal. The cross-sectional image of the body tissue may include a plurality of images obtained by slicing one piece of body tissue along a plurality of different planes. As another example, the image of the body tissue may include an image obtained by imaging the surface of the body tissue with a camera.

The abnormal shape judgment results may include a judgment that an abnormal shape distinguishable from healthy body tissue and caused by unstable functioning, a current disease (e.g., a malignant tumor), or the like of the body tissue is present or not present, and/or a judgment that an abnormal shape that is a precursor to or cause of a future disease of the body tissue is present or not present. The abnormal shape judgment results may include results easily diagnosed by a specialist such as a medical doctor based on the cross-sectional image of the body tissue or the like, or results that are diagnostically confirmed through a more thorough examination by the specialist.

As an example, the learning data may include a plurality of groups of cross-sectional images of lungs and results of a diagnosis confirmed by a medical doctor relating to the presence of lung cancer in these lungs. The learning data may include Boolean data indicating the presence of an anomaly (e.g., 1: Abnormal, 0: Normal) as the judgment result, or may instead include real number data indicating the degree of anomaly (e.g., real number data having a value from 0 to 1 whereby values closer to 1 indicate a greater degree or higher probability of anomaly and values closer to 0 indicate normalcy) as the judgment result. The image acquiring section 110 may supply the extracting section 130 with the images of the body tissue in the acquired learning data and supply the learning processing section 170 with the judgment results.

The learning data may include information relating to abnormal shapes, in addition to the abnormal shape judgment results. For example, the learning data may include information concerning the location where the abnormal shape occurs in the body tissue and/or the size of the abnormal shape.

Next, at S20, the converting section 150 generates the value sequences for the body tissue images included in the learning data. The converting section 150 supplies the learning processing section 170 with the generated value sequences. The process of S20 is described in detail further below.

Next, at S30, the learning processing section 170 trains the neural network that outputs predictions of the abnormal shape judgment results for the body tissue, from the value sequences generated at S20 using the images of the body tissue included in the learning data.

For example, the learning processing section 170 may train the weighting between each node, parameters, and the like for a neural network having a CNN (Convolutional Neural Network) structure including a convolution layer and a pooling layer in at least a portion thereof. The learning processing section 170 may train a neural network separately for each of a plurality of different types of body tissue.

For example, the learning processing section 170 may train a neural network for the lungs by using learning data that includes cross-sectional images of lungs and abnormal shape judgment results for lungs, and may train a neural network for stomachs by using learning data that includes cross-sectional images of stomachs and abnormal shape judgment results for stomachs. The learning processing section 170 may store the trained neural networks in the neural network storage section 180.

Next, at S40, the image acquiring section 110 acquires an image of the body tissue that is an object of the abnormal shape estimation from the image capturing apparatus 20. For example, the image acquiring section 110 acquires an image of body tissue (e.g., a cross-sectional image of the lungs of a patient) for which a diagnosis of an abnormal shape has not yet been made, from the image capturing apparatus 20, which may be a CT apparatus or the like.

Next, at S50, the converting section 150 generates the value sequence for the body tissue image that is the object of the estimation acquired at S40. The converting section 150 supplies the estimating section 190 with the generated value sequence. The process of S50 is described in detail further below.

Next, at S60, the estimating section 190 estimates the abnormal shape of the body tissue by using the neural network to process the value sequence resulting from the conversion from the body tissue image that is the object of the estimation. For example, the estimating section 190 reads a neural network trained at S30 from the neural network storage section 180, and inputs the value sequence into this neural network.

The estimating section 190 may read the neural network for the body tissue image that is the object of the estimation. For example, if a cross-sectional image of lungs is acquired at S40, the estimating section 190 may read the neural network for lungs from the neural network storage section 180.

As a result, the estimating section 190 acquires an abnormal shape estimation result of the body tissue from the neural network as output. In this way, the estimating section 190 can acquire an estimation result indicating whether an abnormal shape (e.g., an abnormal shape resulting from a malignant tumor) is present in the body tissue image that is the object of the estimation. Furthermore, the estimating section 190 may estimate information relating to the abnormal shape, such as the location where the abnormal shape occurs and/or the size of the abnormal shape. The estimating section 190 may output the estimation results to an external device and/or a display connected to the image processing apparatus 10, for example.

Figure 3:
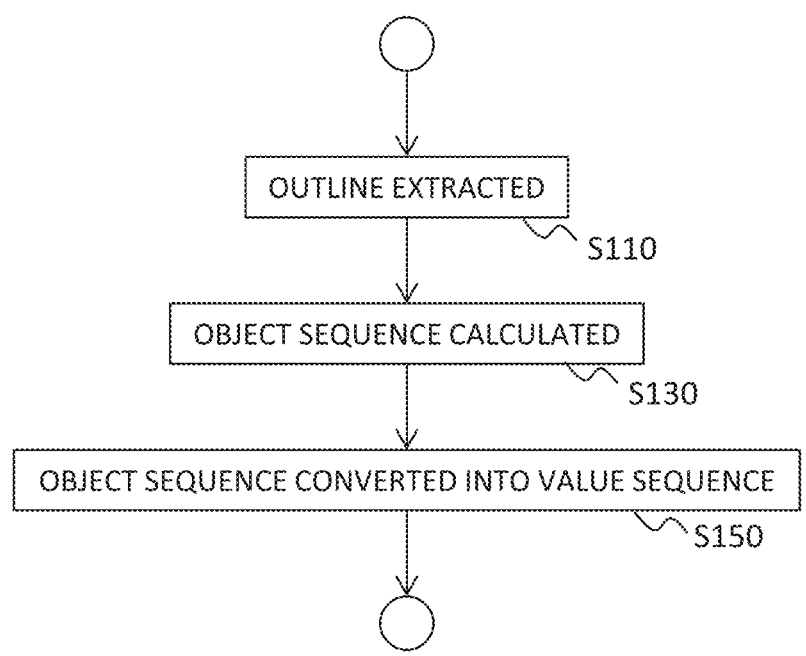
FIG. 3 shows a detailed flow of the value sequence calculation performed in the flow shown in FIG. 2.

FIG. 3 shows a detailed flow of the value sequence calculation performed in the flow shown in FIG. 2. The processes of S20 and S50 in FIG. 2 may be performed according to the processes of S110 to S150 shown in FIG. 3. If the learning data includes a plurality of body tissue images in S20, the image processing apparatus 10 may perform the processes from S110 to S150 for each image to obtain a value sequence for each image.

First, at S110, the extracting section 130 extracts the outline of the body tissue from the body tissue image. For example, for a body tissue image that is in color or gray scale, the extracting section 130 converts the pixels having a brightness greater than or equal to a predetermined threshold value into white pixels and converts the pixels having a brightness less than the predetermined threshold value into black pixels, thereby generating a binary image. As another example, the extracting section 130 may use the P-tile method to generate a binary image based on the ratio of size of the body tissue (e.g., size of lung) and/or the ratio of input background. Next, the extracting section 130 extracts the outline of the body tissue from the generated binary image. As an example, the extracting section 130 extracts the outline of the body tissue by extracting a collection of coordinates of a border line in the binary image of the body tissue.

In another example, the extracting section 130 may detect the outline of the body tissue using the zero-cross technique, an edge detection operator such as Roberts, Sobel, or Prewit, or the like to gather a collection of coordinates on the image from a plurality of points tracing around the outline as the coordinate sequence of the outline. The extracting section 130 supplies the converting section 150 with the outline of the body tissue.

Next, at S130, the sequence calculating section 152 of the converting section 150 calculates the object sequence that is to be the object of the conversion into the value sequence, based on the coordinate sequence for each point tracing around the outline.

For example, the sequence calculating section 152 calculates the object sequence to be relative coordinate values that are relative to reference coordinate values in a one-dimensional direction of the points tracing around the outline of the body tissue. Here, the points tracing around the outline of the body tissue may be points corresponding to pixels included in the outline of the body tissue, and may be a plurality of points that become continuous when moving between pixels of the outline of the body tissue in the ±x direction, the ±y direction, or a combination of the ±x direction and the ±y direction. Furthermore, the points tracing around the outline of the body tissue may be a predetermined number of points corresponding to one of the pixels included in the outline of the body tissue, and may be selected in a manner such that the distance between adjacent points (the distance therebetween along the outline or along a straight line) is within a predetermined range.

The reference coordinate values may be the coordinate values in the x-y plane of predetermined reference points, and coordinate values in a one-dimensional direction from a predetermined origin point among the points tracing around the outline (e.g., coordinate values on the y axis in the x-y plane) may be used as the reference coordinate values. As an example, the origin point may be a point that has the smallest coordinate value in the y-axis direction and the smallest coordinate value in the x-axis direction among the points tracing around the outline. Furthermore, the relative coordinate values may be coordinate values indicating the difference from the reference coordinate value for each point on the outline. In this way, the sequence calculating section 152 calculates the object sequence to be a sequence of coordinate values in a one dimensional direction (e.g., the y-axis direction) of the outline of the body tissue.

Instead, the sequence calculating section 152 may calculate the object sequence to be the distance of each point tracing around the outline of the body tissue relative to a reference point. Here, the sequence calculating section 152 may use, as the reference point, an origin point among the points tracing around the outline of the body tissue, a predetermined point inside the outline of the body tissue, or a predetermined point outside of the body tissue. As an example, the sequence calculating section 152 may identify a point that is the center of mass of the body tissue from the body tissue image (or the outline or the like of the body tissue) and use this center of mass point as the reference point.

Instead of this, the sequence calculating section 152 may calculate the object sequence to be the distance of each point tracing around the outline of the body tissue relative to a reference line. The sequence calculating section 152 may use, as the reference line, a line that passes through the predetermined origin point among the points tracing around the outline. For example, the reference line may be a straight line that passes through the origin point of the outline and has a predetermined slope, such as a straight line passing through the center of mass of the body tissue, a connecting line that connects points on the outline of the body tissue, or a straight line that penetrates through the outline.

Here, the sequence calculating section 152 may calculate the distance from the reference point or the reference line to be a distance with a positive or negative sign (i.e., the value of the difference between the coordinate value of each point and the coordinate value of the reference point or a point on the reference line) or a distance without a positive or negative sign (i.e., the absolute value of the difference between the coordinate value of each point and the coordinate value of the reference point or a point on the reference line).

If a plurality of outlines are obtained from one piece of body tissue (e.g., if a plurality of cross-sectional lung images are captured at different slices for a single patient using CT or the like), the sequence calculating section 152 may string together the object sequences obtained from each outline. The sequence calculating section 152 may perform this stringing together after performing scaling, which is described further below.

The sequence calculating section 152 may calculate the object sequence based on a three-dimensional shape of a surface of the body tissue, instead of the outline of the body tissue in a plane. For example, by layering a plurality of outlines from a plurality of different slices of the body tissue, the sequence calculating section 152 may generate a three-dimensional structure forming a surface of the body tissue and calculate the object sequence to be a sequence of distances of each point included in this three-dimensional structure relative to a reference (e.g., a reference point, reference line, or reference surface).

The sequence calculating section 152 may scale the length of the calculated object sequence to be a reference length. For example, the sequence calculating section 152 may scale the length (e.g., the number of pieces of data) of the object sequence by resampling the object sequence with a predetermined sample number (e.g., 512 samples). The sequence calculating section 152 may perform the resampling using a Fourier series.

In this way, the sequence calculating section 152 can obtain a plurality of object sequences having the same length from a plurality of images of the body tissue having different sizes corresponding to the differences between the images, the number of pixels, and the like, and can improve the accuracy of the learning of the neural network. The sequence calculating section 152 supplies the sequence converting section 154 with the scaled object sequences.

At step S150, the sequence converting section 154 converts the object sequences received from the sequence calculating section 152 into value sequences. The sequence converting section 154 may ignore fluctuation caused by relatively large regions occurring in the object sequence and extract fluctuation occurring in small regions. For example, the sequence converting section 154 may convert the object sequences into value sequences using a series expansion.

The sequence converting section 154 may use a wavelet decomposition, which is an example of a series expansion, to convert the object sequences received from the sequence calculating section 152 into value sequences. Specifically, the sequence converting section 154 may apply a discrete wavelet decomposition one time or a plurality of times to the object sequences received from the sequence calculating section 152 to deconstruct the scaling coefficient into a low-level scaling coefficient and a wavelet decomposition coefficient, thereby converting the object sequences into value sequences.

The sequence converting section 154 may calculate the scaling coefficient and the wavelet decomposition coefficient using the following expressions.

$$S_{j,k} = \Sigma_{n \in Z} \overline{h_{n-2k}} S_{j+1,n}$$ Expression 1:

$$D_{j,k} = \Sigma_{n \in Z} \overline{g_{n-2k}} S_{j+1,n}$$ Expression 2:

Here, j and k respectively represent the level and the shift, $S_{j,k}$ represents the scaling coefficient having the level j and shift k, $D_{j,k}$ represents the wavelet decomposition coefficient having the level j and shift k, $h_{n-2k}$ (overbar) represents the series of scaling function shifted by (n−2k), and $g_{n-2k}$ (overbar) represents the series of wavelet function shifted by (n−2k).

For example, with $S_{j+1,k}$ being the object sequence with a length of 512 received from the sequence calculating section 152, the sequence converting section 154 deconstructs $S_{j+1,k}$ into $S_{j,k}$ (length of 256) and $D_{j,k}$ (length of 256) by applying the wavelet decomposition once, and then obtains $S_{j−1,k}$ (length of 128) and $D_{j−1,k}$ (length of 128) by applying the wavelet decomposition once to $S_{j,k}$. Here, the sequence converting section 154 may acquire the wavelet decomposition coefficient $D_{j−1,k}$ after two deconstructions as the value sequence after conversion.

The sequence converting section 154 may use a variety of series of orthogonal wavelet functions and corresponding scaling functions. For example, the sequence converting section 154 may use a series of Daubechies wavelet functions and corresponding scaling functions, or may use a series of Haar wavelet functions and corresponding scaling functions.

The sequence converting section 154 may supply the value sequence based on the wavelet decomposition coefficient obtained from the wavelet decomposition and the like to a neural network that is currently being trained by the learning processing section 170 based on the learning data or to a neural network that has already been trained and is read from the neural network storage section 180 by the estimating section 190.

In this way, instead of inputting the body tissue image as-is to the neural network, the image processing apparatus 10 converts the body tissue image into a value sequence using the wavelet decomposition and the like and then inputs the result into the neural network. The value sequence resulting from the conversion using wavelet decomposition omits background images that have little relevance for the judgment of abnormal shapes in the body tissue, internal structures of the body tissue, characteristics in large structures of the outline of the body tissue, and the like. On the other hand, the value sequence includes information that can be used to judge the locations of abnormal shapes and characteristics of abnormal shapes in the body tissue, while having a smaller data amount than the body tissue image.

Therefore, with the image processing apparatus 10, it is possible to provide a neural network having a reduced calculation processing amount without losing accuracy for estimating abnormal shapes. In particular, the image processing apparatus 10 can be used effectively in a case where body tissue can be diagnosed as having an anomaly in the internal structure of lungs or the like relatively easily from a binary image of the cross-sectional image but it is difficult to diagnose an anomaly in the surface structure.

As another example of a series expansion, the sequence converting section 154 may use a Fourier series expansion to convert the object sequence into the value sequence. For example, the sequence converting section 154 may acquire, as the value sequence, expansion coefficients obtained by performing a Fourier series expansion one time or a plurality of times (e.g., two times) on the object sequence. As another example, the sequence converting section 154 may acquire, as the value sequence, results obtained by performing an integration or differentiation operation one time or a plurality of times (e.g., two times) on the object sequence. In this way, the sequence converting section 154 can input to the neural network information concerning the locations of abnormal shapes and characteristics of abnormal shapes in the body tissue using a smaller amount of data than is in the body tissue image.

The sequence converting section 154 may input the object sequence as-is into the neural network without performing a conversion. In such a case, the amount of the information input to the neural network is larger than the amount of data of the value sequence resulting from the wavelet conversion but is still smaller than the amount of data in the body tissue image, and therefore it is possible to reduce the amount of computation in the neural network processing by a certain amount.

Figure 4:
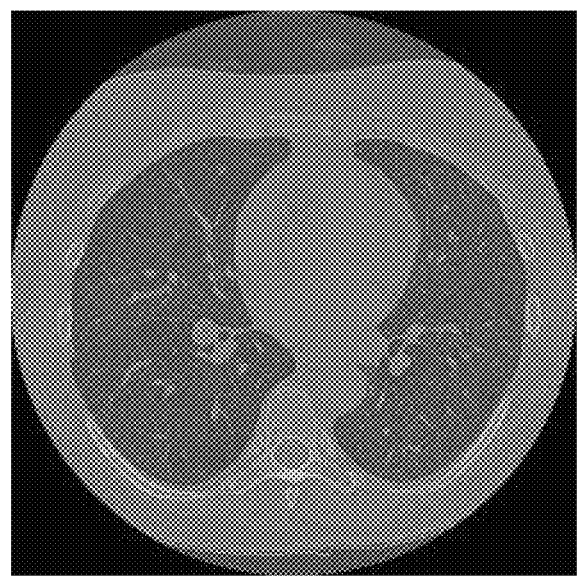
FIG. 4 shows an example body tissue image acquired by an image acquiring section.

FIG. 4 shows an example body tissue image acquired by the image acquiring section 110. For example, in S10 and S40, the image acquiring section 110 may acquire the cross-sectional image of lungs such as shown in FIG. 4 as the body tissue image. In FIG. 4, the two dark grey regions on the left and right sides correspond to the cross sections of the left and right lungs. If the image includes a plurality of organs (such as the left and right lungs in FIG. 4), the image processing apparatus 10 may perform processing on each organ.

If processing is performed on each organ, the image acquiring section 110 may divide the body tissue image according to each organ that is an object of the processing. For example, the image acquiring section 110 may divide the image of FIG. 4 into a left-side image of the left half of the image that includes the left lung and a right-side image of the right half of the image that includes the right lung, and provide the extracting section 130 with the right-side image and the left-side image.

Figure 5:
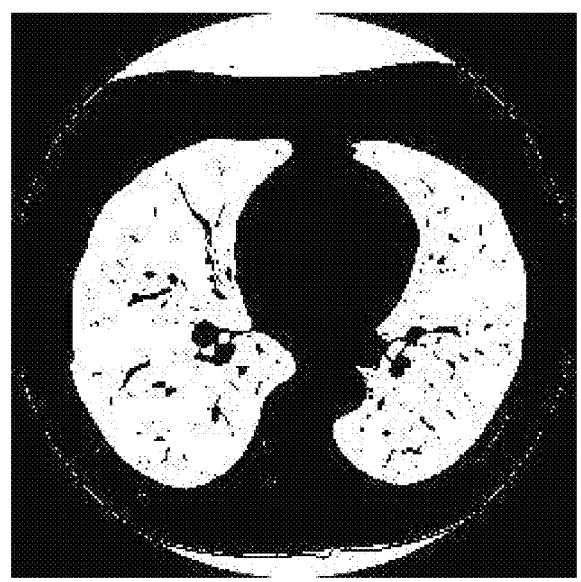
FIG. 5 shows an example binary image of the body tissue shown in FIG. 4.

FIG. 5 shows an example binary image of the body tissue shown in FIG. 4. For example, at S110, the extracting section 130 may generate the binary image of the cross-section of the lungs shown in FIG. 5 from the body tissue image shown in FIG. 4. As an example, for the image shown in FIG. 4, the extracting section 130 may convert the pixels having a brightness greater than or equal to a predetermined threshold value into white pixels and convert pixels having a brightness less than the predetermined threshold value into black pixels, thereby generating the binary image shown in FIG. 5.

Figure 6:
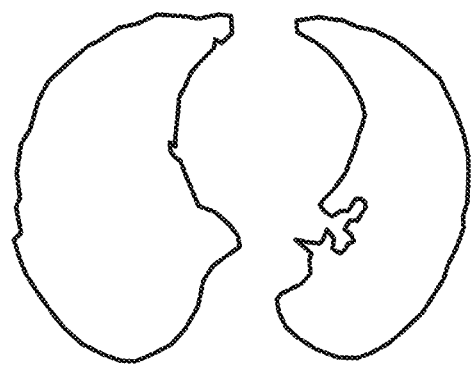
FIG. 6 shows example outlines of the body tissue shown in FIG. 4.

FIG. 6 shows example outlines of the body tissue shown in FIG. 4. For example, at S110, the extracting section 130 may use an edge detection operator or the like to extract the outlines of the right lung and the left lung shown by the thick lines in FIG. 6, from the binary image of the cross section of the lungs shown in FIG. 5.

Figure 7:
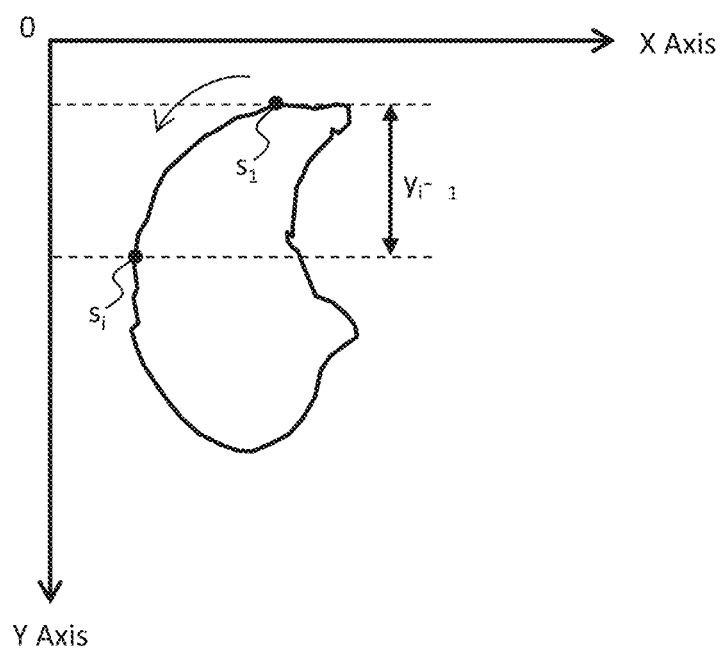
FIG. 7 shows an example method for calculating an object sequence obtained from the image shown in FIG. 4.

FIG. 7 shows an example method for calculating an object sequence obtained from the image shown in FIG. 4. FIG. 7 shows the outline of the left lung from the lungs shown in FIG. 6, and shows a point $s_1$ that is the origin point among the points tracing around the outline. The outline may include n points, which are point $s_2$ (coordinates $x_2$, $y_2$), point $s_3$ (coordinates $x_3$, $y_3$), . . . point $s_n$ (coordinates $x_i$, $y_i$), . . . and point $s_n$ (coordinates $x_n$, $y_n$), and these points are continual in a counter-clockwise direction from the origin point $s_1$ (coordinates $x_1$, $y_1$). For example, at S130, the sequence calculating section 152 may calculate the object sequence to be a sequence of coordinate values relative to $s_1$ in the y-axis direction for each point included in the outline. In other words, the sequence calculating section 152 may acquire, as the object sequence, a result obtained by calculating (0, $y_2$-$y_1$, $y_3$-$y_1$, . . . $y_i$-$y_1$ . . . , $y_n$-$y_1$).

Figure 8:
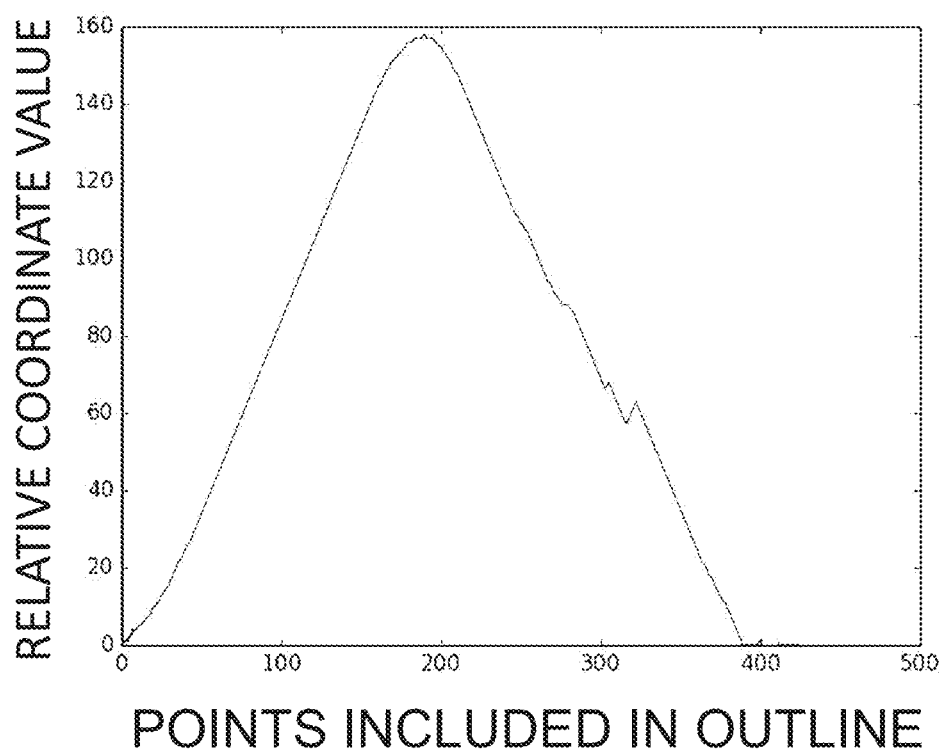
FIG. 8 shows an example object sequence obtained using the method shown in FIG. 7.

FIG. 8 shows an example object sequence obtained using the method shown in FIG. 7. As shown in the drawing, the relative coordinate values of the points in the object sequence form a periodic function that increases and then decreases. Therefore, it is possible to effectively apply a series expansion, such as a wavelet decomposition, to the object sequence. FIG. 8 shows only the object sequence for the left lung, but the sequence calculating section 152 may also calculate the object sequence for the right lung.

Figure 9:
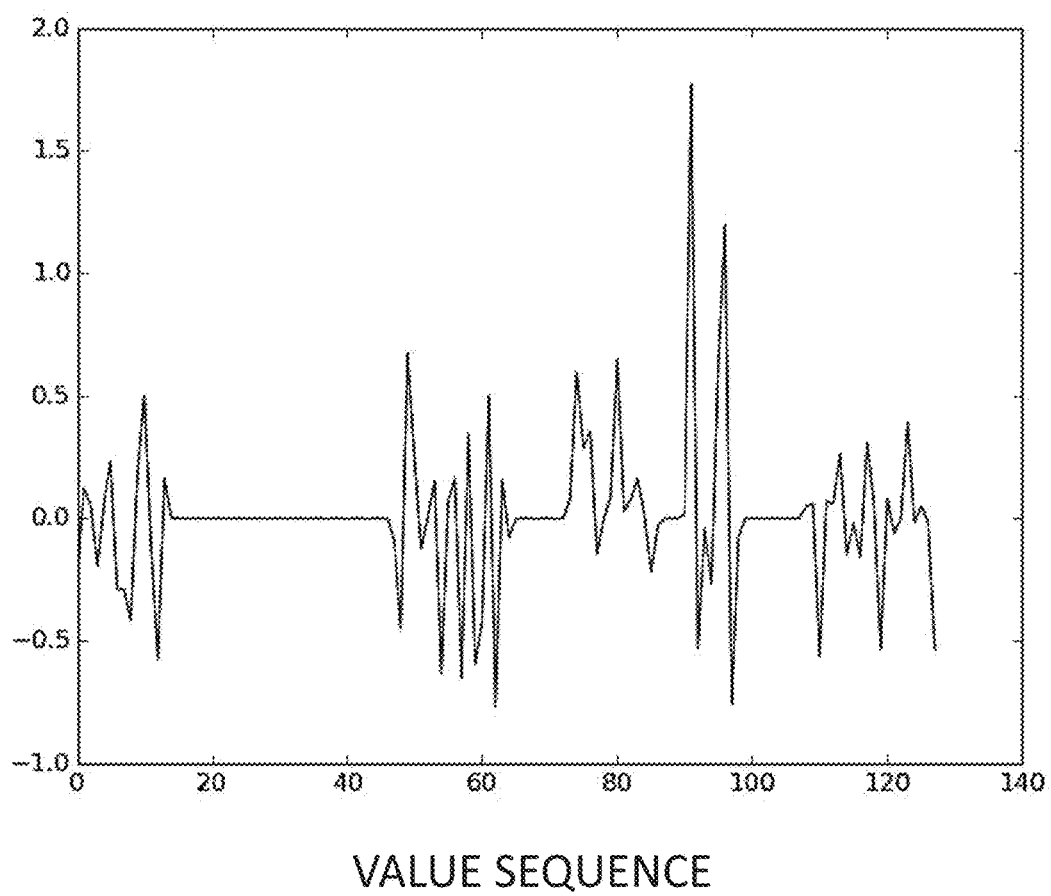
FIG. 9 shows an example value sequence obtained by converting the object sequence shown in FIG. 8.

FIG. 9 shows an example value sequence obtained by converting the object sequence shown in FIG. 8. The value sequence shown in FIG. 9 is obtained by the sequence converting section 154 performing a conversion using a Daubechies wavelet function (N=3). For example, at S150, the sequence converting section 154 may convert the object sequence of the left lung shown in FIG. 8 into the object sequence for the left lung shown in FIG. 9, and convert the object sequence of the right lung into the object sequence for the right lung in the same manner. In this way, the converting section 150 converts the coordinate sequence of the outline of the right lung into the value sequence for the right lung and converts the coordinate sequence of the outline of the left lung into the value sequence for the left lung.

The estimating section 190 may estimate whether a lung disease in contact with the lung outline is present, based on the value sequence resulting from the conversion. For example, the estimating section 190 may estimate an abnormal shape in the right lung by using the neural network that has been trained for the right lung to process the value sequence for the right lung, and estimate an abnormal shape in the left lung by using the neural network that has been trained for the left lung to process the value sequence for the left lung. If body tissue having left-right symmetry or rotational symmetry is being processed, the image processing apparatus 10 may perform an inversion and/or rotation process on each piece of body tissue and then use the same neural network for estimating both pieces of body tissue.

For example, the image processing apparatus 10 may share the value sequence for the right (left) lung with the neural network for the left (right) lung, and in this case, a left-right inversion process may be performed on either the right or left lung (e.g., the process of S110 is performed after performing a right-left inversion of the image of one of the lungs).

Figure 10:
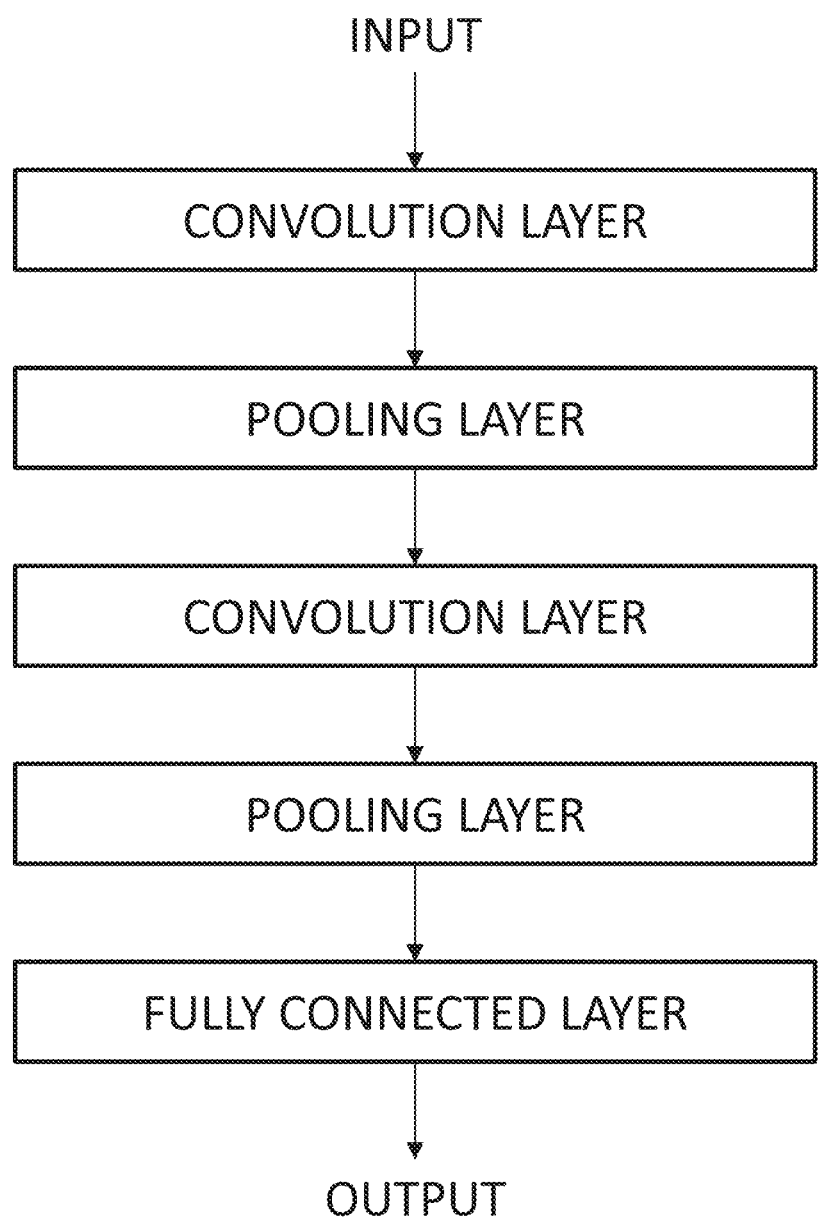
FIG. 10 shows an example layer structure of the neural network for processing by the image processing apparatus.

FIG. 10 shows an example layer structure of the neural network for processing by the image processing apparatus 10. As shown in the drawing, the neural network may include a plurality (e.g., two) groups of convolution layers and pooling layers, and a fully connected layer. The convolution layers may be layers that perform convolution by performing a filtering process on the input, and may include a plurality of neurons corresponding to the plurality of filters. The pooling layers may be layers that apply a filter for extracting a maximum value to the input, and may include a plurality of neurons corresponding to the plurality of filters. The fully connected layer may include a plurality of layers that each have a plurality of neurons, and the neurons may be connected to each other between each layer. The value sequence obtained as a result of the conversion by the converting section 150 is input to the highest convolution layer in FIG. 10, and is processed by the plurality of sets of convolution layers and pooling layers.

The result output from the lowest pooling layer may be input to the fully connected layer. The output result from the fully connected layer may be output as the output of the neural network.

Figure 11:
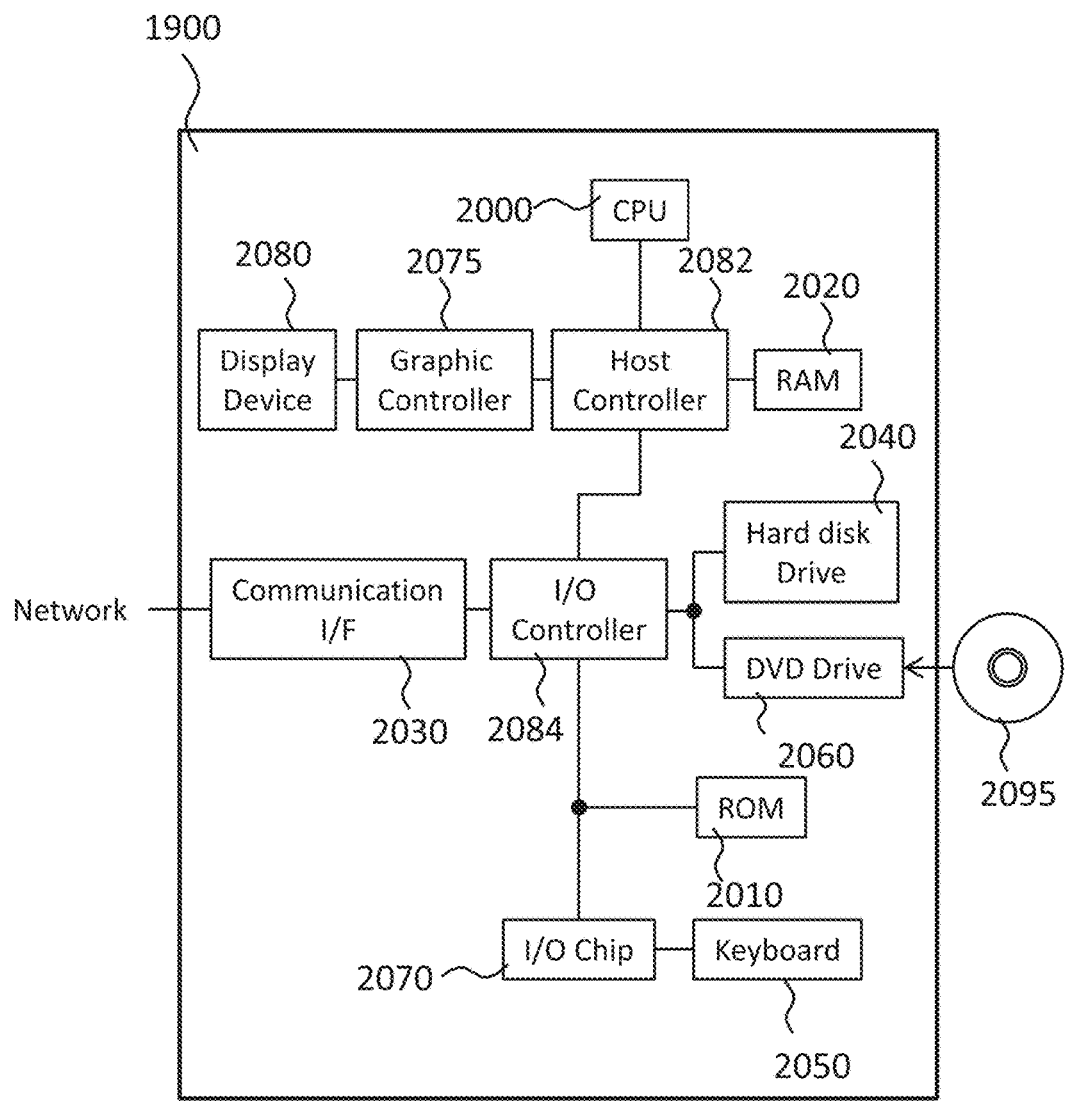
FIG. 11 shows an example hardware configuration of a computer.

FIG. 11 shows an example configuration of a computer 1900 according to an embodiment of the invention. The computer 1900 according to the present embodiment includes a CPU 2000, a RAM 2020, a graphic controller 2075, and a display apparatus or device 2080, which are mutually connected by a host controller 2082. The computer 1900 also includes input/output units such as a communication interface 2030, a hard disk drive 2040, and a DVD-ROM drive 2060, which are connected to the host controller 2082 via an input/output controller 2084. The computer also includes input/output units such as a ROM 2010 and a keyboard 2050, which are connected to the input/output controller 2084 through an input/output chip 2070.

The host controller 2082 connects the RAM 2020 with the CPU 2000 and the graphic controller 2075, which access the RAM 2020 at a high transfer rate. The CPU 2000 operates according to programs stored in the ROM 2010 and the RAM 2020, thereby controlling each unit. The graphic controller 2075 obtains image data generated by the CPU 2000 on a frame buffer or the like provided in the RAM 2020, and causes the image data to be displayed on the display apparatus 2080. Alternatively, the graphic controller 2075 may contain therein a frame buffer or the like for storing image data generated by the CPU 2000.

The input/output controller 2084 connects the host controller 2082 with the communication interface 2030, the hard disk drive 2040, and the DVD-ROM drive 2060, which are relatively high-speed input/output units. The communication interface 2030 communicates with other electronic devices via a network. The hard disk drive 2040 stores programs and data used by the CPU 2000 within the computer 1900. The DVD-ROM drive 2060 reads the programs or the data from the DVD-ROM 2095, and provides the hard disk drive 2040 with the programs or the data via the RAM 2020.

The ROM 2010 and the keyboard 2050 and the input/output chip 2070, which are relatively low-speed input/output units, are connected to the input/output controller 2084. The ROM 2010 stores therein a boot program or the like executed by the computer 1900 at the time of activation, a program depending on the hardware of the computer 1900. The keyboard 2050 inputs text data or commands from a user, and may provide the hard disk drive 2040 with the text data or the commands via the RAM 2020. The input/output chip 2070 connects a keyboard 2050 to an input/output controller 2084, and may connect various input/output units via a parallel port, a serial port, a keyboard port, a mouse port, and the like to the input/output controller 2084.

A program to be stored on the hard disk drive 2040 via the RAM 2020 is provided by a recording medium as the DVD-ROM 2095, and an IC card. The program is read from the recording medium, installed into the hard disk drive 2040 within the computer 1900 via the RAM 2020, and executed in the CPU 2000.

A program that is installed in the computer 1900 may cause the computer 1900 to function as an apparatus, such as the image processing apparatus 10 of FIG. 1. The program may comprise the image acquiring module, the extracting module, the converting module, the sequence calculating module, the sequence converting module, the learning processing module, and the estimating section module. The program or module acts on the CPU 2000, to cause the computer 1900 to function as a section, component, element of the image processing apparatus 10, such as the image acquiring section 110, the extracting section 130, the converting section 150, the sequence calculating section 152, the sequence converting section 154, the learning processing section 170, and the estimating section 190.

The information processing described in these programs is read into the computer 1900 such as the image processing apparatus 10 of FIG. 1, to function as the image acquiring section 110, the extracting section 130, the converting section 150, the sequence calculating section 152, the sequence converting section 154, the learning processing section 170, and the estimating section 190, which is the result of cooperation between the program or module and the above-mentioned various types of hardware resources. Moreover, the image processing apparatus 10 is constituted by realizing the operation or processing of information in accordance with the usage of the computer 1900.

For example, in response to communication between the computer 1900 and an external device, the CPU 2000 may execute a communication program loaded onto the RAM 2020, to instruct communication processing to a communication interface 2030, based on the processing described in the communication program. The communication interface 2030, under control of the CPU 2000, reads the transmission data stored on the transmission buffering region provided in the recording medium, such as a RAM 2020, a hard disk drive 2040, or a DVD-ROM 2095, and transmits the read transmission data to a network, or writes reception data received from a network to a reception buffering region or the like provided on the recording medium. In this way, the communication interface 2030 may exchange transmission/reception data with the recording medium by a DMA (direct memory access) method, or by a configuration that the CPU 2000 reads the data from the recording medium or the communication interface 2030 of a transfer destination, to write the data into the communication interface 2030 or the recording medium of the transfer destination, so as to transfer the transmission/reception data.

In addition, the CPU 2000 may cause all or a necessary portion of the file of the database to be read into the RAM 2020 such as by DMA transfer, the file or the database having been stored in an external recording medium such as the hard disk drive 2040, the DVD-ROM drive 2060 (DVD-ROM 2095) to perform various types of processing onto the data on the RAM 2020. The CPU 2000 may then write back the processed data to the external recording medium via a DMA transfer method or the like. In such processing, the RAM 2020 can be considered to temporarily store the contents of the external recording medium, and so the RAM 2020, the external recording apparatus, and the like are collectively referred to as a memory, a storage section, a recording medium, a computer readable medium, etc. The neural network storage section 180 may be implemented by the external recording apparatus.

For example, the storage section of the image processing apparatus 10 may store data that is received from and/or provided to the image acquiring section 110, the extracting section 130, the converting section 150, the sequence calculating section 152, the sequence converting section 154, the learning processing section 170, and the estimating section 190.

Various types of information, such as various types of programs, data, tables, and databases, may be stored in the recording apparatus, to undergo information processing. Note that the CPU 2000 may also use a part of the RAM 2020 to perform reading/writing thereto on the cache memory. In such an embodiment, the cache is considered to be contained in the RAM 2020, the memory, and/or the recording medium unless noted otherwise, since the cache memory performs part of the function of the RAM 2020.

The CPU 2000 may perform various types of processing, onto the data read from a memory such as the RAM 2020, which includes various types of operations, processing of information, condition judging, search/replace of information, etc., as described in the present embodiment and designated by an instruction sequence of programs, and writes the result back to the memory such as the RAM 2020. For example, if performing condition judging, then the CPU 2000 may judge whether each type of variable shown in the present embodiment is larger, smaller, no smaller than, no greater than, or equal to the other variable or constant, and if the condition judging results in the affirmative (or in the negative), then the process branches to a different instruction sequence, or calls a sub-routine.

In addition, the CPU 2000 may search for information in a file, a database, etc., in the recording medium. For example, if a plurality of entries, each having an attribute value of a first attribute is associated with an attribute value of a second attribute, are stored in a recording apparatus, then the CPU 2000 may search for an entry matching the condition whose attribute value of the first attribute is designated, from among the plurality of entries stored in the recording medium, and reads the attribute value of the second attribute stored in the entry, thereby obtaining the attribute value of the second attribute associated with the first attribute satisfying the predetermined condition.

The above-explained program or module may be stored in an external recording medium. Example recording mediums include a DVD-ROM 2095, as well as an optical recording medium such as a Blu-ray Disk or a CD, a magneto-optic recording medium such as a MO, a tape medium, and a semiconductor memory such as an IC card. In addition, a recording medium such as a hard disk or a RAM provided in a server system connected to a dedicated communication network or the Internet can be used as a recording medium, thereby providing the program to the computer 1900 via the network.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium, which may implement the storage section, may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server.

In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s).

In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In cases where a plurality of elements are provided as example in the description of the present embodiment, elements other than the elements provided as examples may be used. For example, if the description includes a phrase such as "X performs Y using A, B, and C," then X may perform Y using D in addition to A, B, and C.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

LIST OF REFERENCE NUMERALS

10: image processing apparatus, 20: image capturing apparatus, 30: image database, 110: image acquiring section, 130: extracting section, 150: converting section, 152: sequence calculating section, 154: sequence converting section, 170: learning processing section, 180: neural network storage section, 190: estimating section.

What is claimed is:

1. An image processing apparatus comprising:
a computer system comprising:
an image acquiring section that acquires an image of body tissue;
an extracting section that extracts an outline of the body tissue from the image, wherein the outline comprises an ordered plurality of outline points beginning with a reference point, and wherein the reference point and each outline point of the plurality of outline points is defined with a pair of coordinates;
a sequence generating section that generates an object sequence indicating a distance to the reference point for each of the remaining ordered plurality of outline points, wherein each distance is a linear measure from at least one coordinate of an outline point to at least one corresponding coordinate of the reference point;
a sequence converting section that converts the object sequence into a value sequence using a series expansion; and
an estimating section that estimates an abnormal shape of the body tissue by processing the value sequence using a neural network.

2. The image processing apparatus according to claim 1, wherein the sequence generating section calculates the object sequence to be relative coordinate values that are relative to the reference point in a one-dimensional direction for each of the remaining ordered plurality of outline points.

3. The image processing apparatus according to claim 1, wherein the sequence generating section supplies the sequence converting section with a scaled object sequence obtained by scaling a length of the object sequence to be a reference length.

4. The image processing apparatus according to claim 1, wherein the series expansion ignores fluctuations caused by relatively large regions occurring in the object sequence and extracts fluctuations occurring in small regions.

5. The image processing apparatus according to claim 1, wherein the series expansion comprises a wavelet decomposition.

6. The image processing apparatus according to claim 5, wherein the wavelet decomposition is applied to the object sequence a plurality of times.

7. The image processing apparatus according to claim 5, wherein the sequence converting section supplies a neural network with the value sequence based on a wavelet decomposition coefficient obtained by the wavelet decomposition.

8. The image processing apparatus according to claim 1, further comprising:
a learning processing section that trains the neural network using learning data including a plurality of groups of images of body tissue and abnormal shape judgment results.

9. The image processing apparatus according to claim 1, wherein:
the image acquiring section acquires a cross-sectional image of a lung as the image of the body tissue; and
the estimating section estimates whether a lung disease in contact with an outline of the lung is present.

10. The image processing apparatus according to claim 9, wherein:
the extracting section extracts outlines of a right lung and a left lung from the cross-sectional image;
the sequence converting section converts an object sequence generated from the outline of the right lung into a value sequence for the right lung and converts an object sequence generated from the outline of the left lung into a value sequence for the left lung; and
the estimating section estimates an abnormal shape of the right lung by performing processing with a neural network trained for the right lung on the value sequence for the right lung, and estimates an abnormal shape of the left lung by performing processing with a neural network trained for the left lung on the value sequence for the left lung.

11. An image processing method executed by a computer, comprising:

acquiring an image of body tissue;

extracting an outline of the body tissue from the image, wherein the outline comprises an ordered plurality of outline points beginning with a reference point, and wherein the reference point and each outline point of the plurality of outline points is defined with a pair of coordinates;

generating an object sequence indicating a distance to the reference point for each of the remaining ordered plurality of outline points, wherein each distance is a linear measure from at least one coordinate of an outline point to at least one corresponding coordinate of the reference point;

converting the object sequence into a value sequence using a series expansion; and estimating an abnormal shape of the body tissue by processing the value sequence using a neural network.

12. The method of claim 11, wherein the distance to the reference point for each of the remaining ordered plurality of outline points is measured in a one-dimensional direction from the reference point to each outline point.

13. The method of claim 11, wherein the series expansion ignores fluctuations caused by relatively large regions occurring in the object sequence and extracts fluctuations occurring in small regions.

14. The method of claim 11, wherein the series expansion comprises a wavelet decomposition.

15. The method of claim 11, further comprising:

training the neural network using learning data including a plurality of groups of images of body tissue and abnormal shape judgment results.

16. A computer program product comprising a computer readable storage medium having computer readable program code stored thereon, wherein the computer readable program code, when executed by a computer, causes the computer to:

acquire an image of body tissue;

extract an outline of the body tissue from the image, wherein the outline comprises an ordered plurality of outline points beginning with a reference point, and wherein the reference point and each outline point of the plurality of outline points is defined with a pair of coordinates;

generate an object sequence indicating a distance to the reference point for each of the remaining ordered plurality of outline points, wherein each distance is a linear measure from at least one coordinate of an outline point to at least one corresponding coordinate of the reference point;

converting the object sequence into a value sequence using a series expansion; and estimate an abnormal shape of the body tissue by processing the value sequence using a neural network.

17. The computer program product of claim 16, wherein the distance to the reference point for each of the remaining ordered plurality of outline points is measured in a one-dimensional direction from the reference point to each outline point.

18. The computer program product of claim 16, wherein the series expansion ignores fluctuations caused by relatively large regions occurring in the object sequence and extracts fluctuations occurring in small regions.

19. The computer program product of claim 16, wherein the series expansion comprises a wavelet decomposition.

20. The computer program product of claim 16, further comprising:

training the neural network using learning data including a plurality of groups of images of body tissue and abnormal shape judgment results.

* * * * *